United States Patent [19]

Collazo et al.

[11] Patent Number: 5,782,925
[45] Date of Patent: Jul. 21, 1998

[54] KNEE IMPLANT ROTATIONAL ALIGNMENT APPARATUS

[75] Inventors: Carlos E. Collazo; Stuart L. Axelson; Donald G. Eckhoff, all of New York, N.Y.

[73] Assignee: Howmedica Inc., New York, N.Y.

[21] Appl. No.: 965,676

[22] Filed: Nov. 6, 1997

[51] Int. Cl.⁶ ............................................. A61F 2/38
[52] U.S. Cl. ............................................. 623/20
[58] Field of Search ............................... 623/18, 20

[56] References Cited

U.S. PATENT DOCUMENTS

| | | | |
|---|---|---|---|
| 5,480,446 | 1/1996 | Goodfellow | 623/20 |
| 5,683,469 | 11/1997 | Johnson | 623/20 |
| 5,690,636 | 11/1997 | Wildgoose | 623/20 |
| 5,702,463 | 12/1997 | Pothier | 623/20 |
| 5,733,290 | 3/1998 | McCue | 623/20 |
| 5,735,904 | 4/1998 | Pappas | 623/20 |

*Primary Examiner*—Michael J. Milano
*Attorney, Agent, or Firm*—Peter C. Richardson; Lawrence C. Akers; Mark Dryer

[57] ABSTRACT

A knee implant rotational alignment apparatus comprising a non-implantable femoral trial component having substantially the same configuration as a femoral implant, a cooperating tibial articulating trial component having two parallel guide rails protruding from the upper surface thereof, which rails engage with grooves in the lower surface of the femoral trial component, which engagement prevents rotation of the femoral trial component relative to the tibial articulating trial component in a transverse plane but allows flexion and extension rotation of both components, a tibial trial baseplate having an outer periphery substantially identical to the outer periphery of a tibial implant baseplate of corresponding size, which baseplate accommodates a spring clip activator the rotation of which facilitates selection of the rotational alignment of the prosthesis.

4 Claims, 2 Drawing Sheets

5,782,925

KNEE IMPLANT ROTATIONAL ALIGNMENT APPARATUS

FIELD OF THE INVENTION

This invention relates to a knee implant rotational alignment apparatus. More particularly, the invention is concerned with a specially designed trialling apparatus comprising a femoral trial, a tibial articulating trial, a tibial trial baseplate and anchoring bone nails. The invention also provides a method for attaining the proper rotational alignment of a knee prosthesis using the aforesaid apparatus.

BACKGROUND OF THE INVENTION

The kinematics of the natural knee are such that flexion and extension thereof causes the femur to rotate in the transverse plane relative to the tibia. During Total Knee Arthroplasty, rotational placement and alignment of the femoral and tibial implant components is very important for the restoration of the joint's kinematics and optimization of the wear characteristics of the implant. Failure to optimize the rotational alignment of the implant may result in premature wear and other complications associated with misalignment known in the orthopaedic community. Accordingly, a system which can easily, accurately and systematically determine the amount of rotation which occurs between the femoral and tibial components during any chosen degree of flexion/extension would assist a surgeon to select the optimum rotational position of the implant.

The present invention provides the surgeon with an apparatus for assessing joint rotation and establishing the cumulative amount of external and internal rotation which occurs between the femoral and tibial components relative to each other during any given degree of flexion and/or extension of the knee. More specifically, it is a trialing system comprising a femoral trial(s), a tibial articulating trial(s), a tibial base plate(s) and anchoring bone nails, preferably two.

SUMMARY OF THE INVENTION

In accordance with the invention there is provided a knee implant rotational alignment apparatus which comprises a non-implantable femoral trial component having substantially the same configuration as a femoral implant comprising a left condyle and a right condyle, each condyle having an upper concave surface and a lower convex surface, which femoral trial component contains two longitudinal grooves parallel to each other cut into the lower surface of the left and right condyle, respectively; a tibial articulating trial component having an upper surface, a lower surface and a forward edge, two parallel guide rails protruding from the upper surface, which rails engage with said grooves in the lower surface of the femoral trial component, which engagement prevents rotation of the femoral trial component relative to the tibial articulating trial component in a transverse plane but allows flexion and extension rotation of both components, an internal bore positioned substantially centrally in said lower surface of the tibial articulating trial component and a groove in said lower surface extending from said bore to the forward edge of said component; a tibial trial baseplate having an outer periphery substantially identical to the outer periphery of a tibial implant baseplate of corresponding size, an upper surface, a lower surface and a forward edge, which upper surface has a central bore connected to a recessed cavity defined by two side walls at an acute angle to each other and extending to the forward edge, which bore and cavity accommodates a spring clip activator comprising a protruding hub with a cylindrical central bore and a connected rotatable arm extending along said recessed cavity whereby the angle of rotation is restricted by the side walls of the cavity, which arm terminates in an anterior tab which protrudes through an aperture in the forward edge of said tibial trial baseplate and is sandwiched between two spring clips located in a radially shaped pocket set in the upper surface of the baseplate adjacent the forward edge, said spring clip activator being attached to the tibial trial baseplate through a post located in the central bore of said protruding hub, which post has a lower portion which is press fitted into a bore between the upper surface and lower surface of the baseplate, said baseplate being releasably connected to said tibial articulating trial by locating said hub and integral arm in said bore and groove, respectively, in the lower surface of said tibial articulating trial.

When the trial components are placed on the patient the tibial trial baseplate is temporarily secured to the tibia with bone nails, preferably two bone nails which are driven through holes in the tibial trial baseplate and into the bone to ensure adequate stability. Accordingly the apparatus of the invention also includes two bone nails and holes are provided in the baseplate between the protruding hub and the periphery to accommodate the nails and two hemispherical grooves are located on each side of the bore in the lower surface of the tibial articulating trial component to provide adequate clearance for the head of each bone nail.

In a preferred embodiment of the apparatus the post located in the central bore of the hub comprises an upper cylindrical portion which rotatably fits into the bore of the hub and a lower cylindrical portion having a diameter smaller than that of the upper portion, which lower portion is press fitted into a small diameter bore descending concentrically from the central bore into said lower surface of the baseplate.

The invention also provides a method for establishing the optimal rotational position of a tibial component in relation to a femoral component in a knee prosthesis, which comprises the steps of selecting femoral and tibial trial components as described above of the same size as the implant components, preparing the femur and tibia according to a standard procedure, fitting the femoral trial on the femur, placing the tibial trail baseplate on the prepared tibia, rotationally aligning the baseplate to attain the maximum implant coverage of the resected tibial plateau and temporarily securing the baseplate to the bone with two bone nails, placing the tibial articulating trial component on the tibial trial baseplate and adjusting the position thereof to ensure that the protruding hub and connected arm are fully engaged in the internal bore and extending groove, respectively, in the lower surface of the tibial articulating trial component, rotating the tibial articulating trial component so that the outer periphery thereof is aligned with the outer periphery of the tibial trial baseplate, thereafter bringing the spring clips together and marking the rotational centre of the tibial trial on the bone, engaging the femoral trial component with the tibial articulating trial component, rotating the tibial articulating trial component about the axis of the hub causing equal rotation of the spring clip activator and consequent equal rotation of the spring clips, thereby establishing the mean centre of rotation to facilitate selection of the rotational alignment of the prosthesis.

BRIEF DESCRIPTION OF THE DRAWINGS

The invention will be more particularly described with reference to a preferred embodiment illustrated in the accompanying drawings, in which.

DETAILED DESCRIPTION OF THE INVENTION

Figure 1:
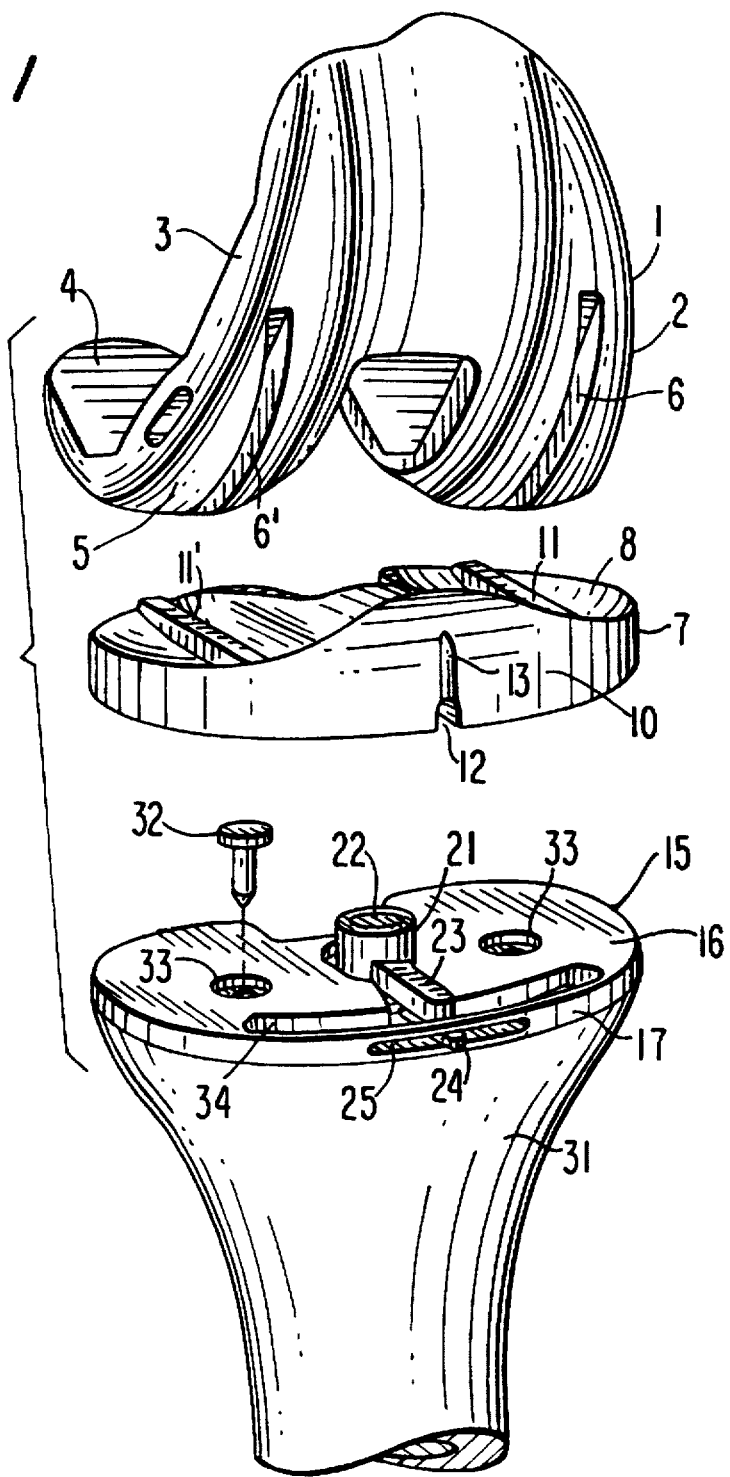
FIG. 1 is an exploded perspective view of the trialling apparatus of the invention.

FIG. 1 of the accompanying drawings is an exploded perspective view of a particularly preferred embodiment of the apparatus of the invention and shows the main components thereof.

The apparatus comprises a femoral trial component 1 which is a substantially identical, non-implantable representation of the femoral implant comprising a left condyle 2 and a right condyle 3, each condyle having an upper concave surface 4 and a lower convex surface 5, with the exception that the trial component contains two longitudinal grooves 6,6' parallel to each other cut into the lower surface of the left and right condyle, respectively.

Figure 2:
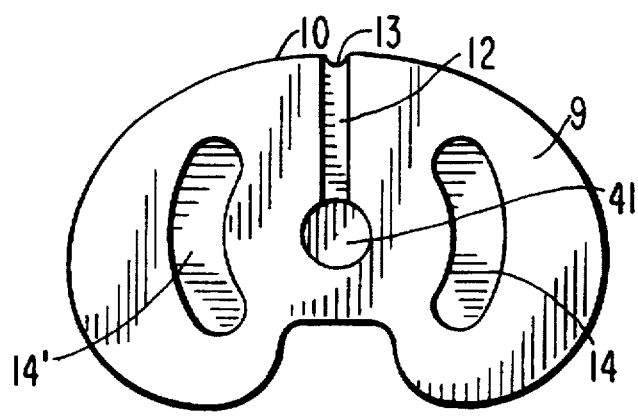
FIG. 2 is a plan view of the lower surface of the tibial articulating trial of the apparatus of FIG. 1.

The apparatus also comprises a tibial articulating trial component 7 having an upper surface 8, a lower surface 9 (see FIG. 2), a forward edge 10 and two parallel guide rails 11, 11' protruding from the upper surface, which rails engage with the grooves 6, 6', respectively, in the lower surface of the femoral trial component when the two components are brought into contact with each other. The engagement prevents rotation of the femoral trial component relative to the tibial articulating trial component in a transverse plane but allows flexion and extension rotation of both components. As shown in FIG. 2, an internal bore 41 is positioned substantially centrally in the lower surface of the tibial articulating trial component and a groove 12 extends in the lower surface from the bore to the forward edge of the component. A "V" notch 13 in the forward edge of the component extends from the end of the groove to the upper surface. Two hemispherical grooves 14, 14' are located on each side of the bore 41 in the lower surface of the tibial articulating trial component to provide adequate clearance for the heads of bone nails which are used to temporarily secure a tibial trial baseplate to a patient's tibia as described hereinafter.

Figure 3:
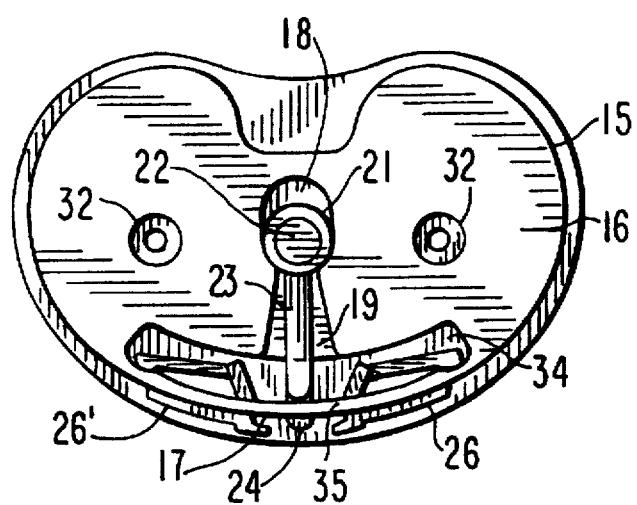
FIG. 3 is a plan view of the upper surface of the tibial trial baseplate of the apparatus showing the spring clip activator.
Figure 4:
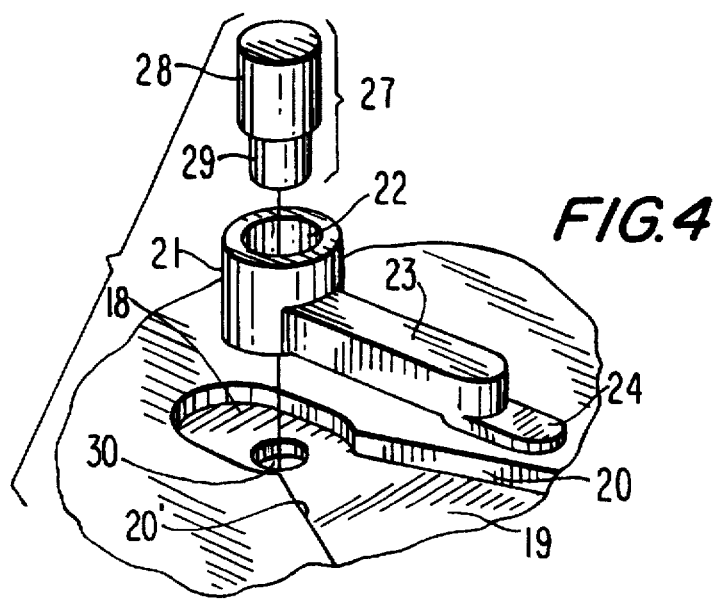
FIG. 4 is an enlarged partial cutaway view of part of the activator of FIG. 3.

The apparatus of the invention further comprises a tibial trial baseplate 15 as illustrated in FIG. 1, FIG. 3 and FIG. 4. The tibial trial baseplate 15 has an outer periphery substantially identical to the outer periphery of a tibial implant baseplate of corresponding size, an upper surface 16, a lower surface (not shown), and a forward edge 17. The upper surface has a central bore 18 connected to a recessed cavity 19 defined by two side walls 20, 20' at an acute angle to each other and extending to the forward edge 17. The bore 18 and recessed cavity 19 accommodates a spring clip activator which comprises a protruding hub 21 with a cylindrical central bore 22 and a connected rotatable arm 23 which arm extends along the recessed cavity 19 whereby the angle of rotation is restricted by the side walls of the cavity. The arm 23 terminates in an anterior tab 24 which protrudes through an aperture 25 in the forward edge of the tibial trial baseplate. The anterior tab and the arm itself are sandwiched between two spring clips 26, 26' (see FIG. 3) located in a radially shaped pocket 34 set in the upper surface of the baseplate adjacent the forward edge. The spring clip activator is attached to the tibial trial baseplate through a post 27 located in the central bore 22 of the protruding hub 21. In the preferred embodiment the post 27 comprises an upper cylindrical portion 28 which rotatably fits into the bore 22 of the hub and a lower cylindrical portion 29 which has a smaller diameter than that of the upper portion. The lower portion is press fitted into a small diameter bore 30 descending concentrically from the central bore 18 into the lower surface of the baseplate. The upper cylindrical portion 28 of the post 27 is slightly smaller in diameter than the bore 22, thus allowing radial rotation of the spring clip activator about the axis of the post 27 while at the same time preventing disassociation of both components. The lateral sides of the recessed cavity 19 limit the amount of rotation of the spring clip activator.

When the trial components are placed on a patient the tibial trial baseplate 15 is temporarily secured to the tibia 31 with bone nails, and a preferred embodiment of the apparatus includes two bone nails 32 (only one shown in FIG. 1). The bone nails are driven through holes 33 in the tibial trial baseplate and into the bone to ensure adequate stability. The two hemispherical grooves 14, 14' in the lower surface of the tibial articulating trial component illustrated in FIG. 2 provide adequate clearance for the head of each bone nail when the components are placed together. Also the internal bore 41 and connected groove 12 in the lower surface of the tibial articulating trial component engage with the protruding hub 21 and connected rotatable arm 23, respectively, on the spring clip activator. Preferably the protruding hub 21 is circular in cross-section and the arm 23 is rectangular in cross-section. The engaging bore 41 and groove 12 are similarly circular and rectangular in cross-section, respectively.

The two spring clips 26, 26' are factory assembled to the tibial trial baseplate 15 through the aperture 25 in the forward edge 17 of the tibial trial baseplate. The radially shaped pocket 34 set in the upper surface of the tibial trial baseplate is machined so that a ridge 35 of uniform wall thickness is formed between the forward edge of the tibial trial baseplate and the outer wall of the pocket 34. The tension provided by the spring clips 26, 26' act on the ridge 35 in such a way as to prevent the spring clips from moving freely. However, by applying a sufficient force both spring clips may be moved in a radial direction following the curvature of the outer radius of the forward edge 17 of the tibial trial baseplate. The anterior tab 24 of the arm 23 protrudes through the aperture 25 and is sandwiched between the two spring clips 26, 26'. This positioning enables the tab to activate or push the spring clips outwardly. Hence rotation of the spring clip activator in either direction causes equal rotation of the spring clips.

The apparatus of the invention provides a surgeon with an improved method for selecting the rotational alignment of a knee prosthesis. To perform the method using the apparatus of the invention, the patient's femur and tibia are prepared to receive the prosthesis and the proper sized femoral trial component is selected and fitted on to the prepared femur. The proper sized tibial trial baseplate is then selected and placed on the prepared tibia using known techniques which rely on:—a) anatomic bone structures used as reference landmarks, b) attainment of the maximum implant coverage of the resected tibial plateau, and c) the clinical judgment and experience of the surgeon. After initial placement, the tibial trial baseplate is temporarily secured to the tibia with two bone nails which are driven through holes in the tibial trial baseplate and into the bone to ensure adequate stability.

After placement of the femoral and tibial trial components onto the femur and tibia, respectively, the tibial articulating trial component is placed on the tibial trial baseplate and adjusted to ensure that the protruding hub and connected rotatable arm of the spring clip activator are fully engaged in the mating bore and mating groove, respectively, in the lower surface of the tibial articulating trial component. When the stated components are assembled, the tibial articulating trial is rotated so that the outer periphery thereof is aligned with the outer periphery of the tibial trial baseplate, which has a substantially identical peripheral geometry. At this time the surgeon brings both spring clips together and transfers the location of the "V" notch to the bone using a suitable marking instrument, preferably an electrosurgical device known in the art as a "bovie". The location of the "V" notch represents the rotational centre of the tibial trial based solely on visual orientation.

Following the steps described hereinabove, the surgeon engages the femoral trial component with the tibial articulating trial and proceeds by flexing the patient's knee through any desired degree of flexion/extension. Since the femoral trial component is fully constrained by the positive engagement of the mating grooves and guide rails, the rotation experienced by the femur causes the tibial articulating trial component to rotate the same amount. Rotation of the tibial articulating trial component takes place about the axis of the protruding hub of the spring clip activator and does not cause rotational displacement of the underlying tibial trial baseplate since the latter is fixed to the bone with two bone nails.

Rotation of the tibial articulating trial component cause equal rotation of the spring clip activator. Similarly, rotation of the spring clip activator causes equal rotation of the spring clips. Since the spring clip activator is not mechanically fastened to the spring clips, rotation of the spring clip activator simply pushes the spring clips in the direction of rotation and leaves them in that position when the direction of rotation of the spring clip activator is reversed. This allows the maximum rotation that takes place throughout any degree of flexion/extension to be recorded, represented as the minimum distance between the spring clips.

The midpoint of the minimum distance between the spring clips represents the mean centre of rotation of the particular range of motion selected during this procedure. The surgeon proceeds by marking the tibia with a bovie in the location representing said midpoint between the spring clips. This new centre established through flexion/extension of the knee may or may not coincide with the first mark previously made on the tibia which represented the centre of rotational alignment made by visual observations and clinical judgment. Thus the surgeon has an added option in selecting the rotational alignment of the prosthesis.

We claim:

1. A knee implant rotational alignment apparatus which comprises a non-implantable femoral trial component having substantially the same configuration as a femoral implant comprising a left condyle and a right condyle, each condyle having an upper concave surface and a lower convex surface, which femoral trial component contains two longitudinal grooves parallel to each other cut into the lower surface of the left and right condyle, respectively; a tibial articulating trial component having an upper surface, a lower surface and a forward edge, two parallel guide rails protruding from the upper surface, which rails engage with said grooves in the lower surface of the femoral trial component, which engagement prevents rotation of the femoral trial component relative to the tibial articulating trial component in a transverse plane but allows flexion and extension rotation of both components, an internal bore positioned substantially centrally in said lower surface of the tibial articulating trial component and a groove in said lower surface extending from said bore to the forward edge of said component; a tibial trial baseplate having an outer periphery substantially identical to the outer periphery of a tibial implant baseplate of corresponding size, an upper surface, a lower surface and a forward edge, which upper surface has a central bore connected to a recessed cavity defined by two side walls at an acute angle to each other and extending to the forward edge, which bore and cavity accommodates a spring clip activator comprising a protruding hub with a cylindrical central bore and a connected rotatable arm extending along said recessed cavity whereby the angle of rotation is restricted by the side walls of the cavity, which arm terminates in an anterior tab which protrudes through an aperture in the forward edge of said tibial trial baseplate and is sandwiched between two spring clips located in a radially shaped pocket set in the upper surface of the baseplate adjacent the forward edge, said spring clip activator being attached to the tibial trial baseplate through a post located in the central bore of said protruding hub, which post has a lower portion which is press fitted into a bore between the upper surface and lower surface of the baseplate, said baseplate being releasably connected to said tibial articulating trial by locating said hub and integral arm in said bore and groove, respectively, in the lower surface of said tibial articulating trial.

2. An apparatus according to claim 1 which also includes two bone nails, two holes in the baseplate between the protruding hub and the periphery to accommodate the nails and two hemispherical grooves located on each side of the bore in the lower surface of the tibial articulating trial component to provide adequate clearance for the head of each bone nail.

3. An apparatus according to claim 1, in which the post located in the central bore of the hub comprises an upper cylindrical portion which rotatably fits into the bore of the hub and a lower cylindrical portion having a diameter smaller than that of the upper portion, which lower portion is press fitted into a small diameter bore descending concentrically from the central bore into said lower surface of the baseplate.

4. A method for establishing the optimal rotational position of a tibial component in relation to a femoral component in a knee prosthesis, which comprises the steps of selecting an apparatus according to claim 1 comprising femoral and tibial trial components of the same size as the implant components, preparing the femur and tibia according to a standard procedure, fitting the femoral trial on the femur, placing the tibial trail baseplate on the prepared tibia, rotationally aligning the baseplate to attain the maximum implant coverage of the resected tibial plateau and temporarily securing the baseplate to the bone with two bone nails, placing the tibial articulating trial component on the tibial trial baseplate and adjusting the position thereof to ensure that the protruding hub and connected arm are fully engaged in the internal bore and extending groove, respectively, in the lower surface of the tibial articulating trial component, rotating the tibial articulating trial component so that the outer periphery thereof is aligned with the outer periphery of the tibial trial baseplate, thereafter bringing the spring clips together and marking the rotational center of the tibial trial on the bone, engaging the femoral trial component with the tibial articulating trial component, rotating the tibial articulating trial component about the axis of the hub causing equal rotation of the spring clip activator and consequent equal rotation of the spring clips, thereby establishing the mean centre of rotation to facilitate selection of the rotational alignment of the prosthesis.

* * * * *